United States Patent

Onishi et al.

[11] Patent Number: 5,862,626
[45] Date of Patent: Jan. 26, 1999

[54] PROCESS FOR PRODUCING TUBER

[75] Inventors: Noboru Onishi; Kunihiro Hayashida; Kanji Mamiya, all of Kitsuregawa-machi, Japan

[73] Assignee: Kirin Beer Kabushiki Kaisha, Japan

[21] Appl. No.: 773,603
[22] PCT Filed: Mar. 25, 1991
[86] PCT No.: PCT/JP91/00382
   § 371 Date: Nov. 20, 1991
   § 102(e) Date: Nov. 20, 1991
[87] PCT Pub. No.: WO91/14359
   PCT Pub. Date: Oct. 3, 1991

[30] Foreign Application Priority Data

Mar. 23, 1990 [JP] Japan ................... 2-74762
Mar. 23, 1990 [JP] Japan ................... 2-74763

[51] Int. Cl.⁶ ........................................ A01H 4/00
[52] U.S. Cl. ........................................ 47/58; 435/240.45
[58] Field of Search ............... 47/58; 435/240.4, 435/240.44, 240.45

[56] References Cited

U.S. PATENT DOCUMENTS

| | | | |
|---|---|---|---|
| 4,466,216 | 8/1984 | Howard | 435/244 X |
| 4,857,464 | 8/1989 | Weathers et al. | 435/240.4 X |
| 5,034,327 | 7/1991 | Takayama et al. | 435/240.4 |
| 5,047,343 | 9/1991 | Foyer et al. | 435/240.45 |

FOREIGN PATENT DOCUMENTS

| | | |
|---|---|---|
| A 0 293 488 | of 0000 | European Pat. Off. . |
| 1-285117 | 11/1984 | Japan . |
| 63-500104 | 11/1987 | Japan . |
| 1-304826 | 5/1988 | Japan . |
| 2016921 | 1/1990 | Japan . |
| WO A 8 802 213 | of 0000 | WIPO . |

OTHER PUBLICATIONS

Estrada et al., "Induction of in vitro tubers in a broad range of potato genotypes," Plant Cell Tissue Org. Cul., vol. 7, pp. 3–10 (1986).
Wang, P.J. and Hu, C.Y., "In vitro mass tuberization and virus–free seed–potato production in Taiwan," Am. Potato J., vol. 59, pp. 33–37 (1982).
Rosell et al., "In vitro mass tuberization as a contribution to potato micropropagation," Potato Research, vol. 30, pp. 111–116 (1987).
Hussey, G. and Stacey, N.J., "Factors affecting the formation of in vitro tubers of potato (*Solanum tuberosum* L.)" Ann.Bot., vol. 53, pp. 565–578 (1984).
Akita, M. and Takayama, S. "Mass propogation of potato tubers using jar fermentor techniques," Acta Horticult., vol. 230, pp. 55–61 (1988).
Lakso et al., "Carbon dioxide enrichment for stmulation of growth in in vitro propagated grapevines after transfer from culture," J. Amer. Soc. Hort. Sci., vol. 111, pp. 634–638.

(List continued on next page.)

*Primary Examiner*—James R. Feyrer
*Attorney, Agent, or Firm*—James C. Weseman, Esq.; The Law Offices of James C. Weseman

[57] ABSTRACT

This invention provides a process for easy and large-scale production of tubers from plants belonging to the genus Solanum, wherein the improvement resides in that tubers are formed with high efficiency by exposing stolons and shoots, elongated in a liquid phase under a carbon dioxide-applied condition during light periods in a shoot propagation step, to a gaseous phase in a subsequent tuber formation step, and that tubers are formed in a large number not only in a boundary medium surface area but also in a gaseous phase area distant from the medium surface by culturing the stolons and shoots during the tuber formation step in a culture jar with aeration of the gaseous phase. By employing such culture steps and conditions, tuber forming efficiency and quality of the produced tubers are improved.

8 Claims, 3 Drawing Sheets

OTHER PUBLICATIONS

Kozai, T. and Iwanami, Y., "Effects of $CO_2$ enrichment and sucrose concentration under high photon fluxes on plantlet growth of carnation (*Dianthus caryophyllus* L.) in tissue culture during the preparation stage," J. Japan Soc. Hort. Sci., vol. 57, pp. 279–288 (1988).

Kozai et al., "Multiplication of potato plantlets in vitro with sugar free medium under high photosynthetic photon flux," Acta Horticult., vol. 230, pp. 121–127 (1988).

Kozai et al., Supplement I of J. Japan Soc. Hort. Sci., vol. 58 (1989) in Japanese: pp. 244–245.

Arteca et al., "Changes in carbon fixation, tuberization, and growth induced by $CO_2$ application to the root zone of potato plants," Science, vol. 205, pp. 1279–1280 (1979).

Paterson, D.R., "Effect of CO enriched internal atmosphere on tuberization and growth of the potato," J.Amer.Soc.Hort.Sci., vol. 100, pp. 431–434 (1975).

Kishor, P.B.K. et al., "Regeneration of plants from long–term cultures of *Oryza sativa* L.", Plant Cell Rpts. (1986) 5:391–393.

Kishor, P.B. K. et al., "Osmoregulation and Organogensis in Callus Tissues of Rice," Indian J. of Exper. Bio., vol. 24, Nov. 1986, pp. 700–702.

Plant Tissue Culture: Theory and Practice, edited by S.S. Bhojwani and M.K. Razdan pp. 92, 94.

Wang, P.J. and Hu, C.Y., "Potato tissue culture and its applications in agriculture," Potato Physiology, chapter 15, pp. 503–577 (1985).

Yamada, Y. and Sato, F., "Selection for photoautotrophic cells," Evans, D.A., et al., –eds–Handbook of plant cell culture: vol. 1, Techniques for propagation and breeding, Macmillan Publishing Co., chapter 1, p. 492 (1983).

Miki, T., "Atmosphere free germ multiplication potato propagate rapid seedling," World Patents Index, Week 7419, 24 May 1972, AN 74–255331V.

Miller, S.A. and Lipschutz, "Potato", Ammirato, P.V. et al. –eds–, Handbook of plant cell culture: vol. 3, Crop species, Macmillan Publishing Co., Chapter 11, pp. 291–326.

Cary, JW., American Potato Journal, vol. 63, No. 11 (1986), pp. 619–627, Effects of relative humidity, oxygen and carbon dioxide on initiation and early development of stolons and tubers.

Muigo–Castel, et al., (1974) "Effect of carbon Dioxide and Ethylene on Fiberization of Isolated Potato Stolons Cultured *in Vitro*" Plant Physiol., vol. 53, pp. 798–801.

PROCESS FOR PRODUCING TUBER

FIELD OF THE INVENTION

This invention relates to a process for producing tubers of plants belonging to the genus Solanum.

PRIOR ART

Worldwide, vegetative propagation is mainly used for the production of the potato. A tuber (vegetative propagation organ) is planted, and as it grows, stolons develop from subterranean nodes (axillary buds) and the tips of the stolons become swollen, forming new tubers. (Stolon is a kind of a lateral branch but, while a terrestrial lateral branch shows negative geotropism and has similar morphology to the main stem, the subterranean stolon shows plagiotropism and elongates horizontally or in a slightly downward fashion and has no distinct leaves). These new potato tubers are then used as next generation seed potatoes or materials to be processed, or consumed as food. One seed tuber typically reproduces about 10 potato tubers.

In the field of the production of potato tubers to utilize vegetative propagation, various viral infections mediated mainly by aphides become serious problems. In seed propagating crops such as rice, barley, wheat and corn, virus infection of plants does not cause serious problems because most viruses do not transmit to the next generation through seeds formed by fertilization even if the plants are infected with a virus. In contrast, if potato plants are once infected with a virus, the virus not only multiplies in the plant itself but also transmits to the seed potatoes of the next generation. The potato plants are propagated mainly by potato tubers without fertilization, as described above, the yield of potato tubers incurres serious damage by the infection. Since it is almost impossible to remove virus particles from the tissues of the infected potato plant under natural conditions, cultivation systems that minimize viral infection have been utilized worldwide to reduce damage of viral disease. These systems basically depend on a supply of virus-free seed potatoes because, as described above, any effort to prevent viral infection becomes meaningless if a potato tuber to be planted is once infected with a virus.

The supply of such virus-free seed potatoes, varied with the area of the cultivation, has been carried out generally through the following steps; (1) creating virus-free individuals by means of an apical meristem culture, (2) acclimatizing the created virus-free individuals and preparing small tubers by means of potting, (3) cultivating these small tubers in a greenhouse in order to harvest mature tubers, (4) cultivating and re-harvesting the obtained mature tubers in the field, and (5) repeating the field cultivation step (3 to 5 times), depending on the required number of the virus-free potato tubers. Though the current worldwide production of the virus-free seed potatoes is carried out as described above, the establishment of the high standard of cultivation techniques and quarantine organization is still essential for the safe operation of the supply system because, in the current system, there is a certain danger of viral re-infection in the field. Consequently, the establishment of simpler and safer systems for the supply of seed potatoes has been awaited.

As one of these desirable systems, utilization of potato tubers prepared by means of tissue culture techniques under sterile conditions has been contemplated in various fields. In this system, potato tubers are prepared in vitro from virus-free individuals obtained by an apical meristem culture without exposing them to the exterior atmosphere in a greenhouse or in the field, and the resulting tubers are used as seed potatoes directly or after cultivating them once or twice in the field. Such potato tubers formed by the current in vitro techniques under sterile conditions are called "microtubers" because of their markedly small sizes (1 g or less in weight and 5 to 10 mm in diameter in most cases) as compared to the usual tubers (50 to 300 g).

The tubers have the following advantages. (1) These tubers are completely free from diseases including viral diseases because they are prepared from virus-free plantlets under sterile conditions. (2) Since the tubers are prepared under tissue culture conditions, their qualities and quantities are not affected by natural conditions and, therefore, they can be produced all the year round. (3) Because it is possible to use these microtubers as seed potatoes directly or after one or two times of cultivation in the field, a danger of viral reinfection or other disease injuries is negligible or is markedly small as compared with those prepared by any other prior art system. (4) They can be transported easily in large quantities because of their small size.

The tubers having such advantages are prepared under sterile conditions by a culturing process which is generally divided into the following two steps (Estrada et al., *Plant Cell Tiss. Org. Cult.*, vol. 7, pp. 3–10, 1986; Wang, P. J. and C. Y. Hu, *Am. Potato J.*, vol. 59, pp. 33–37, 1982; Rosell et al., *Potato Research*, vol. 30, pp. 111–116, 1987; and Hussey, G. and N. J. Stacey, *Ann. Bot.*, vol. 53, pp. 565–578, 1984).

Shoot Propagation Step: In this step, pieces of potato plants are allowed to produce new shoots to multiply axillary buds which are required in the next tuberization step. For this purpose, pieces of potato plants are cultured at 20° to 25° C. for generally 3 to 5 weeks under a certain photoperiodic condition on an agar medium or in a liquid medium which contains a typical plant tissue culture medium as a basal medium supplemented with 1 to 3% of sucrose as a carbon source and, if necessary, with a low concentration of plant hormone. When planted under these conditions described above, a plant piece having at least one bud grows into a plantlet having small but similar terrestrial morphology to that of a naturally grown plant. The growth of the plant pieces or plantlets is usually accompanied by the root formation but not by tuberization.

Tuber Formation Step: The shoots grown in the above step are transferred in a aforementioned basal medium supplemented with a more increased concentration of sucrose (5 to 10%) and, if necessary, with a plant hormone such as cytokinin and a plant growth retardant. When a shoot propagation step is carried out in a liquid medium, formation of tubers is simply done by changing the liquid medium. These shoots are cultured at 15° to 25° C. generally for 4 to 8 weeks, under dark conditions, but sometimes under a low illuminance of 100 to 500 Lux or under a short photoperiodic condition. Under the conditions described above, tubers are formed directly on axillary buds on the shoots or stems elongated from the axillary buds.

The process for the production of microtubers in the prior art, however, has not been applied in practical use except for the preservation and distribution of genetic resources, because the process of the prior art has a low tuber-inducing efficiency and is not applicable to a large scale production of tubers, which results in a high production cost.

To overcome these disadvantages, several attempts have been made as disclosed in Japanese Patent Application No. 63-500104 (International Publication No. WO 88/04136) and in *Acta Horticult.* (Akita, M. and S. Takayama, vol. 230, pp. 55–61, 1988). Since most tubers are formed only in the boundary area between a liquid medium and a gaseous phase according to these improved methods described above, it is necessary to lower the surface level of the medium gradually during the tuberization process in order to induce tubers efficiently on the entire elongated plant bodies. To induce tubers efficiently, a large volume of medium is used to submerge most part of the plant in the medium according to one of these improved methods and, when tubers start forming near the boundary area, a portion of the medium is removed artificially to promote the plant to form additional tubers around the lowered surface of the medium. A sufficient number of tubers are obtained by repeating this artificial medium-removing step. According to another improved method, the surface level of a tuberization medium is lowered gradually by forced evaporation of the medium by passing a large volume of air (0.8 to 2.2 vvm) through a liquid phase.

In these methods, however, most medium is used only for induction of tubers and not for their development. In other words, added carbon sources and other nutrients are not used economically, thereby entailing a difficulty in further reduction of the production cost. In particular, artificial removal of a tuberization medium requires a number of operations and increases a possible chance of contamination. Also, most axillary buds that form tubers are formed in a gaseous phase during the shoot propagation step, and shoots formed in a medium are hardly utilized. In addition, according to our follow-up study of these processes, tubers formed near the boundary area of the medium surface have shown enlarged lenticels or epidermal injuries in some potato varieties and are not suitable for storage and for planting in the field.

Problems to be solved by the Invention

A primary object of the present invention is to provide an improved process for the production of potato tubers, in which the aforementioned problems involved in the prior art are solved. Specifically, the object of the present invention is to provide a process for an easy and large scale production of potato tubers having properties suitable for storage and cultivation.

Means for Overcoming the Problems

The present inventors have investigated intensively to attain the aforementioned objects and have successfully found that an application of carbon dioxide during light periods in the shoot propagation step stimulates (1) active induction and propagation of stolons while no stolon is induced under culture conditions of certain prior art, (2) efficient induction and propagation of thick stolons under currently used stolon inducing conditions, (3) more active induction and propagation of stolons even under long day and low temperature in dark periods, and (4) that, by exposing the elongated stolons and shoots in a liquid phase under carbon dioxide application conditions to the gaseous phase during the tuber formation step, tubers can be formed synchronously and efficiently on both exposed stolons and shoots within a short period of time. The present inventors have also found unexpectedly that (5) numerous tubers can be formed not only in an area close to a medium surface but also in an area in a gaseous phase distant from the medium surface regardless of the presence or absence of stolons or exposed shoots to the gaseous phase when a direct aeration is applyed to the gaseous phase in a culture vessel during the tuber formation step, and that, as a result, tuberization efficiency and quality of tubers can be improved. Furthermore, the present inventors have found that (6) quantitatively and qualitatively better tubers can be produced by combining the above findings (4) and (5). The present invention has been accomplished on the basis of the findings described above.

Several examples in which carbon dioxide is applied to a plant culture have been disclosed [e.g., Japanese Patent Application Laid-Open-to-Public Publication No. 1-285117, Japanese Patent Application Laid-Open-to-Public Publication No. 1-304826, Japanese Patent Application Laid-Open-to-Public Publication No. 2-16921, Lakso et al., *J. Amer. Soc. Hort. Sci.*, 111: pp. 634–638, 1986 and Kozai, T. and Y. Iwanami., *J. Japan. Soc. Hort. Sci.*, 57: pp. 279–288, 1988]. The primary objects of these prior art processes, however, are to increase the growth rate of cultured plants, to enhance root formation and to improve survival ability at the time of acclimation by changing their growth mode from heterotropism into photo-autotropism. Carbon dioxide is also used to optimize photosynthesis of plantlets. Furthermore, the plantlets are expected to be grown into the mature individuals having the same morphology and properties as those of plants grown under natural conditions. There has been no report on induction of plantlets having new morphological properties by application of carbon dioxide and the use of new plantlets that cannot be obtained under natural conditions.

Application of carbon dioxide in potato plant cultivation has been reported by Kozai et al. in *Acta Horticult.*, 230: pp. 121–127, 1988 and by Kozai et al. in Supplement I of *J. Japan. Soc. Hort. Sci.*, 58: pp. 244–245, 1989, but there has been no report on carbon dioxide application to tuber formation. The objects of their reports are similar to those of the aforementioned prior art: they contemplated to produce plantlets having properties (i.e., easy acclimation to natural conditions) and the same terrestrial morphology as that of naturally grown plants by imparting photo-autotropism to the plantlets. In their methods, however, induction and propagation of stolons and tuber formation are not observed, nor is the possibility of any of these phenomena suggested. In addition, a relatively low concentration of carbon dioxide (mostly 1000 ppm (0.1%) or below) is used in order to optimize photosynthesis of the plantlets under specific culture conditions.

It has also been reported that application of carbon dioxide to root systems (Arteca et al., *Science*, vol. 205, pp. 1279–1280, 1979) or directly to typical tubers (D. R. Paterson, *J. Amer. Soc. Hort. Sci.*, vol. 100, pp. 431–434, 1975) promotes growth of terrestrial parts and elongation and development of stolons and increases the number of tubers per stolon and the yield of tubers. In these cases, the treated plant is considered to belong to the same morphological category as a potato plant grown under natural conditions because the treated plant clearly has the morphological difference between the growing part of the shoot and the tuber formation part. In addition, a high concentration of carbon dioxide (45% in the Arteca et al report and 80% in the Paterson's report) was applied to specific organs (root system in the Arteca et al case and tubers in the Paterson's case) for a short period of time (12 hours in both reports).

Under plant tissue culture conditions, formation of stolons has been observed mostly under short-day conditions. Such stolons, however, have not been positively used for the production of tubers because they have generally a thin body, low induction efficiency and low tuberization ability. In the natural environment, elongation of potato stolons is said to be generally enhanced under long-day conditions. Occasional elongation of stolons and formation of tubers have been observed in culture under long-day conditions (Hussey, G. and N. J. Stacey, supra). However, effective induction and propagation of stolons or the use of the stolons for the production of tubers has been unknown. There has been no report on tuber production culture using a combination of low temperature in dark periods and long-day conditions.

Figure 1:
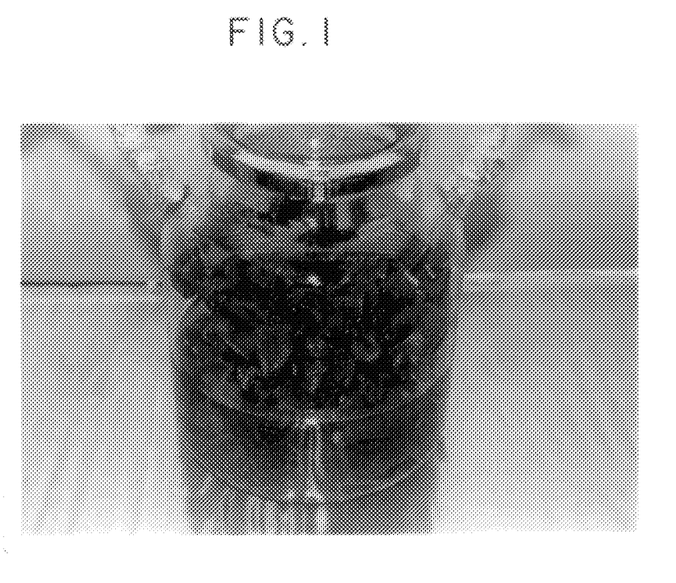
FIG. 1 is a photograph showing a shoot propagation according to a prior art process (a method used for the control plot in Example 2).
Figure 2:
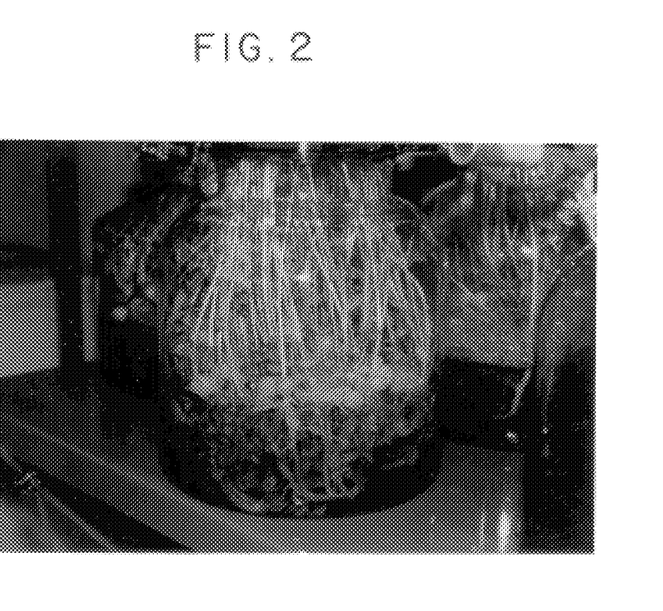
FIG. 2 is a photograph showing a tuber formation according to prior art process (a method used in the control plot in Example 2).
Figure 3:
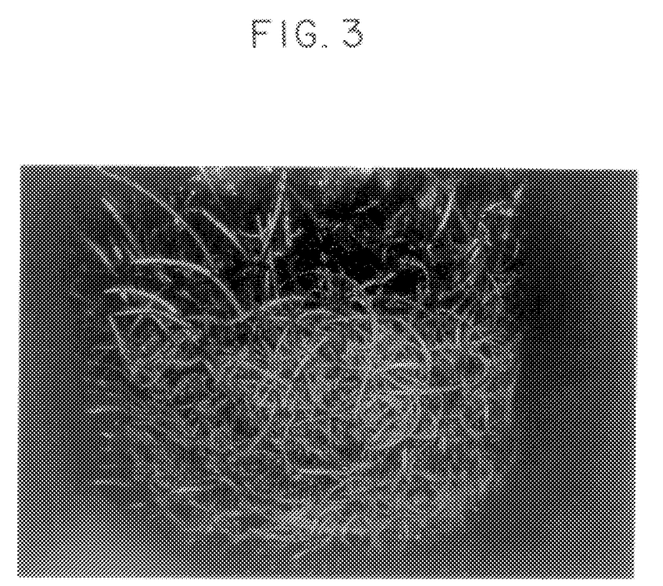
FIG. 3 is a photograph showing induction and propagation of stolons by carbon dioxide application, as described in Example 6.
Figure 4:
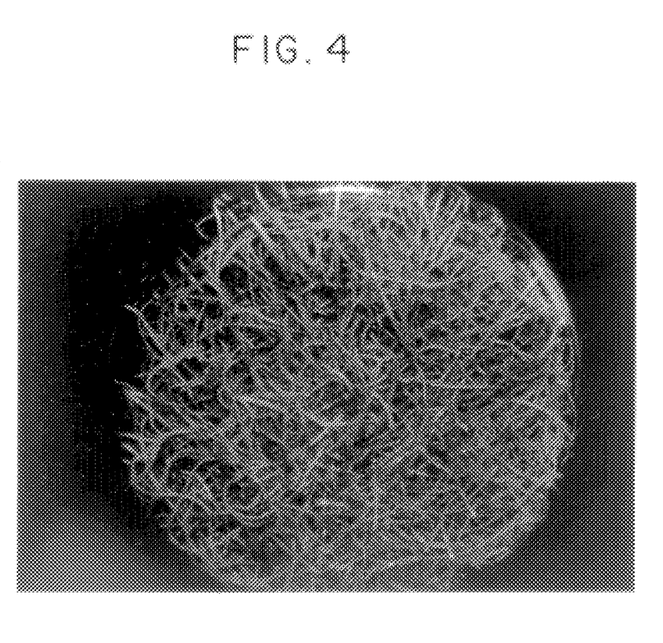
FIG. 4 is a photograph taken from the bottom of a culture jar, showing induction and propagation of stolons by carbon dioxide application, as described in Example 6.

In general, stolons elongate only in the area of root systems under soil in the natural environment and are hardly formed under typical culture conditions (mainly long-day conditions) except for some cases in which a small number of thin stolons are formed under certain conditions (mainly short-day conditions). The present inventors have found that a plant form useful for the production of tubers can be induced by an application of carbon dioxide during light periods. Such treatment has promoted a plant to actively differentiate and develop more thickened stolons from the top to the bottom of the plant. In some cases, well-developed stolons has formed a unique mass structure (FIGS. 3 and 4).

Figure 5:
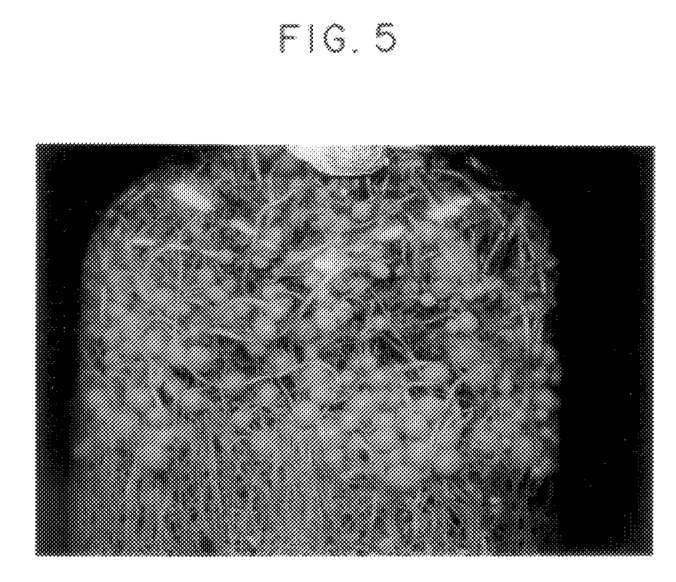
FIG. 5 is a photograph showing tuber formation on stolons and stems induced and propagated by carbon dioxide application, as described in Example 4.

It has also been found that stolons and axillary buds of stems, which are formed by the process of the present invention, possess higher tuberization ability, as compared with those obtained by the prior art process. The stolons and stems, which elongated in a liquid phase under carbon dioxide application conditions and were then cultured by exposing to a gaseous phase at the tuber formation step, formed tubers efficiently (synchronously, in a short period of time, high yield) in a gaseous phase at the tuber formation step, independent of the distance from the medium surface. The tuber formation are especially numerous when the culturing is carried out under conditions that the stolons and stems elongate in the gaseous phase during a carbon dioxide application period and are then exposed to the gaseous phase during a tuber formation period. Under such conditions, tubers mainly form from the direct thickening of the tip of these stolons, but many tubers also forms directly from the axillary buds of the stolons and stems or from the newly developed stolons. As a result, almost entire part of a successful plant, from its top to bottom, is covered with tubers, thus showing a remarkably different morphology from naturally grown potato plants, a morphology which is characterized by a mixed presence of shoot and tuber formation part on the plant (FIG. 5). Such a phenomenon is also markedly different from that of prior art processes in which axillary buds are formed in a gaseous phase during the shoot propagation step and most tuberization occur on axillary buds in an area close to a medium boundary in a culture jar at the tuber formation step.

The process of the present invention discloses induction and propagation of stolons that eventually leads to a formation of a unique stolon/tuber mass. In conventional plant culture systems such as a carbon dioxide application method and a tuber formation method, the induction and propagation of stolons and induction of the unique mass have not been reported or even expected. As described above, the process of the invention has greatly improved tuberization efficiency. In addition, the tuberization efficiency per unit sugar is also greatly improved according to the process of the present invention since a tuber induction medium, which generally requires a considerabley higher concentration of sucrose than that in a shoot propagation medium, is markedly smaller amount as compared with that of the prior art process .

In the method of prior art processes, no morphological change of cultured plants has been contemplated: where a gaseous phase in a culture vessel is directly aerated with air without carbon dioxide enrichment, the cultured plants are attempted to be grown by promoting photosynthesis or to improve their survival ability after acclimation. In addition, there are no report on a direct aeration to a gaseous phase during the tuber formation step.

On the contrary, according to the process of the present invention, direct aeration to a gaseous phase in a culture vessel at the time of tuberization showed unexpected effects on induction of a characteristic plant morphology which is different from that of naturally growing plants and on tuberization efficiency which is considerably improved. When a gaseous phase in a culture vessel is appropriately aerated, a large number of tubers form on the gaseous-phase-exposed portion of a plant from its top to medium-contacting parts, without significant lowering of the medium surface level and independent of the medium volume. In some cases, tubers form directly on axillary buds elongated during the shoot propagation step or on new stems or stolons elongated from the axillary buds during the tuber formation step. When direct aeration of the gaseous phase is carried out properly, tubers are formed under relatively dry conditions because humidity around the tuber-attaching sites becomes low. According to the process of the present invention, high quality tubers are produced which have higher dry matter, lesser enlarged lenticels and epidermal injury than those obtained by the prior art process.

Such a tuber formation manner in the present invention can be regarded as a novel phenomenon, because a similar tuber formation manner has not been found under the culture conditions of the prior art without artificially lowering the medium surface level to a great extent in a culture vessel.

Figure 6:
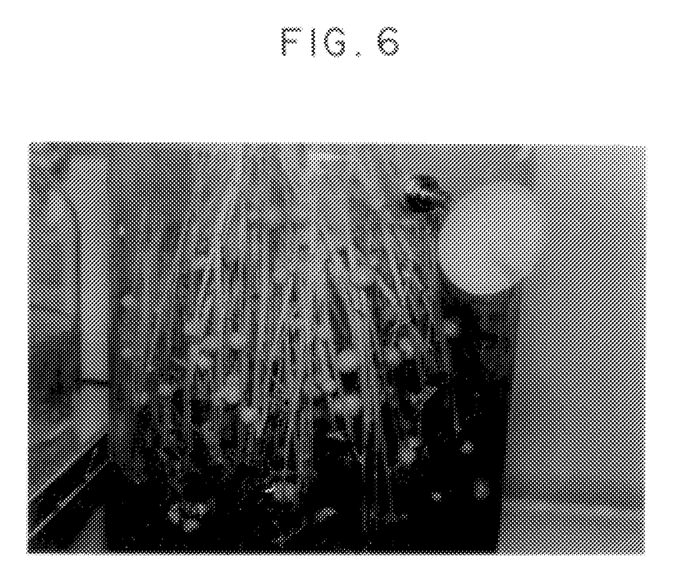
FIG. 6 is a photograph showing tuber formation by an aeration in the gaseous phase in a culture jar, as described in Example 1.

The novel technique of the invention at the tuber formation step are effective regardless the culture method of plants used at the shoot propagation step (FIG. 6). Most excellent results can be obtained when tuber formation is combined with the aforementioned tuber forming method using carbon dioxide application (FIG. 5).

The present invention provides a process for the production of tubers from a tuber-forming plant belonging to the genus Solanum, which comprises the following processes 1 to 5.

1. A process for producing tubers from a tuber-forming plant belonging to the genus Solanum, which comprises a shoot propagation step and a tuber formation step in a culture vessel, characterized in that:
   (1) during said shoot propagation step, a plant piece having at least one bud is cultured in a liquid medium containing at least a carbon source and inorganic salts under a culture condition in which carbon dioxide is applied to the plant piece during at least a part of a light period to induce and propagate shoots and stolons, and
   (2) during said tuber formation step, the stolons are cultured in a liquid medium containing at least a carbon source under a condition that at least a part of the stolons formed in the liquid medium in said shoot propagation step is exposed to a gaseous phase.
2. The process for producing tubers according to process 1 wherein culture is carried out under an aerated condition that reduces the relative humidity of the gaseous phase during said tuber formation step.
3. The process for producing tubers according to process 1 wherein 0.1–30% (v/v) carbon dioxide is applied.
4. The process for producing tubers according to process 1 wherein air enriched with 0.1–30% (v/v) carbon dioxide is applied to the vessel at an aeration rate from 0.0001 to 1 volume per minute per volume of the vessel capacity.
5. A process for producing tubers from a tuber-forming plant belonging to the genus Solanum, which comprises a shoot propagation step and a tuber formation step in a culture vessel, characterized in that, culture is carried out under an aerated condition that reduces the relative humidity of the gaseous phase during said tuber formation step.

The following describes the present invention in detail. The processes 1 and 5 are defined as a first embodiment and a second embodiment, respectively, as a matter of convenience.

The term "stolon" as used herein includes the following three types of stems (cf. FIGS. 3 and 4).

(1) A stem which has similar morphology to that of a stolon of a naturally growing plant (long internode in comparison with terrestrial lateral branch, hooks on its tip portion, no chloroplast included and therefore rather white in color, a trace of or repressed leaf development on each node) and exhibits an apparent plagiotropism (its direction of elongation is horizontal or obliquely downward).

(2) A stem which has almost the same morphology as that of the type (1) stolon, but has slightly developed leaves containing chloroplasts and is partly reddish in color in some cases. It also shows plagiotropism.

(3) A stem which has the same morphology as that of the type (2) stolon but elongates upwardly. The development of the leaves in a medium or in a gaseous phase is very slow or repressed.

Plants used in the present invention include all the species belonging to the genus Solanum and having tuber-forming ability. Illustrative examples of these plants include a potato cultivar (*Solanum tuberosum*), *S. demissum, S. acaule, S. stoloniferum, S. phureja* and the like, of which the potato cultivar is well known.

A culture vessel used in the process of the present invention may be any type of culture jar equipped with an aeration system for the supply of air or carbon dioxide-enriched air, preferably a jar suitable for aeration in both liquid and gaseous phases. Any typical air-permeable vessels or caps for plant tissue culture can be also used instead of a culture jar. A conical flask, a cylindrical culture bottle or a polycarbonate culture vessel equipped with a cap having improved gas permeability can be generally used.

The first embodiment of the present invention comprises two steps, a shoot propagation step (A) in which shoots and stolons are induced and propagated by growing plantlets through application of carbon dioxide during light periods, and a tuber formation step (B) in which tubers are formed on stolons and axillary buds on stems of plants. These steps are separately described in the following. The second embodiment of the present invention will be described in the description of the step (B). Other embodiments of the invention such as the processes 2, 3, and 4, will also be described in relation to the steps (A) and (B).

Shoot Propagation Step (A)

Any aseptically maintained plant may be used in this step, but the plant completely free from viral infection and other diseases is more preferable. Such plants may be obtained by an apical meristem culture of buds formed on individuals grown in the field or on tubers after harvest. A plant piece having at least one bud is used as a planting material. The planting material does not necessarily have roots. Preferably, however, a plantlet having several buds and roots may be used as a planting material. The planting material may be planted in a density of 1 to 50 pieces per 1 liter medium. The plantlet or plant piece without stolons may be used, but the plantlet or plant piece with stolons may be more preferably used. When a plantlet or a plant piece without stolons is used as a planting material, a certain period of time is required to "induce" stolons and, subsequently, the vigorous growth of stolons occurs from the induced stolons and shoots. On the contrary, when a plantlet or a plant piece with stolons is used, the growth of stolons starts immediately after planting the plantlet or plant piece because induction of stolons has already been completed. A plantlet or a plant piece with stolons helps reduce culture time. A stolon itself or part of a stolon having at least one bud may also be used as a planting material. In the shoot propagation step, shoots and stolons are induced and propagated and, advantageously, their tuber-forming ability is improved.

A basal medium (typical medium for plant tissue culture) supplemented with 1 to 3% of sucrose as a carbon source may be used as a culture medium. Illustrative examples of such basal media include Murashige & Skoog medium (referred to as "MS medium" hereinafter), Linsmaier & Skoog medium, White medium, Schenk & Hildebrandt medium and the like, of which MS medium is most useful. Compositions and related factors of these prior art media are disclosed in "*Plant Cell and Tissue Culture*" (Harada and Komamine, pp. 390–391, 1984; published by Rikogakusha). Glucose, maltose, molasses or the like may also be used as a carbon source instead of sucrose.

0.001 to 10 ppm of plant growth regulators may be added to a basal medium. Plant growth regulators include plant hormones such as 1-naphthaleneacetic acid (NAA), indol-3-acetic acid (IAA), 2,4-dichlorophenoxyacetic acid (2,4-D), indole-3-butyric acid (IBA), gibberellic acid ($GA_3$), 6-benzyladenine (BA), kinetin and the like, and plant growth retardants such as cycocel (CCC), ancymidol and the like. In particular, $GA_3$ has an elongating effect on stolons in many cases. A volume of a medium may be preferably 30% or more by volume of a culture jar or of a vessel to be used, which is not strictly limited, because (1) stolons are induced more easily and frequently in a medium than outside of the medium, (2) these stolons elongate vigorously in a liquid phase and form branches and produce additional stolons from the formed branches, (3) not only stolons but also stems elongate and form branches vigorously in a liquid phase, (4) such stems contain a large number of axillary buds, and (5) tubers are produced efficiently from stolons and axillary buds on stems when these stolons and stems are formed in a liquid phase under certain conditions that will be described below. The pH of a culture medium may be adjusted within the range from 4 to 8, preferably from 5 to 7.

In addition to these basic culture conditions, photoperiodic condition, temperature and irradiation direction are closely associated with induction and propagation of stolons. These conditions are described below.

1. Long-Day Conditions

Generally, stolons are not easily induced under long-day conditions, 14 hours or longer day light at 20° to 25° C., which are usually applied to potato tissue culture, although the photoperiodic sensitivity of each cultivar affects inducibility of stolons. Even if induced, stolons elongate as terrestrial stems or foliar stems but not as stolons. Stolons are vigorously induced and propagated by an application of carbon dioxide under the following long-day conditions: (1) continuous photoperiodic conditions or (2) conditions that temperature in dark periods is 15° C. or below.

Culture temperature in the case of (1) may be within the range from 15° to 30° C., preferably from 17° to 22° C., while temperature in the case (2) may be within the range from 15° to 30° C., preferably from 17° to 25° C. during light periods, and from 5° to 15° C., preferably from 8° to 12° C. during dark periods. In both cases, (1) and (2), illuminance may be controlled within the range from 1,000 to 20,000 lux, preferably from 3,000 to 8,000 lux. In the case of (2), duration of a light period may be within the range from 14 to 20 hours, preferably from 15 to 18 hours. Since some stolons induced by the process of the present invention elongate toward the direction of illuminated light, illumination may be preferably made from sideways or bottom side directions to increase the number of stolons in a liquid phase.

2. Short-Day Conditions

In many cultivars, stolons are generally induced and elongate under a short-day culture condition (12 hours or shorter). These stolons, however, are generally thin in shape, small in numbers and less efficient at the time of tuber formation step, when they are obtained without application of carbon dioxide. On the contrary, when a carbon dioxide application is employed under the short-day condition, the stolons become markedly thick, and the number of the stolons increases and tuberization rate at the time of the following tuber formation step is also improved. Light periods may be within the range from 6 to 12 hours, preferably from 8 to 10 hours. Since the growth of plants itself is apt to slow down under short-day conditions, plants cultured in advance under a long-day condition for a certain period of time may be also used. Culture temperature may be within the range from 5° to 30° C., preferably from 17° to 25° C. In addition, when temperature in dark periods is lowered to 5° to 15° C., more noticeable effect may be obtained. Illuminance may be within the range from 1,000 to 20,000 lux, preferably from 3,000 to 8,000 lux. Stolons induced in this manner are apt to exhibit positive geotropism or plagiogeotropism. Illumination may be made from any direction, but preferably from sideways or bottom side directions.

Carbon dioxide may be applied in the same manner under both long-day and short-day conditions. When a culture jar is used for culture, a gaseous phase and/or a liquid phase in the jar is aerated with air enriched with carbon dioxide. When a small culture vessel is used for culture, culture is carried out in a carbon-dioxide-enriched atmosphere. A carbon dioxide concentration in the culture jar for aeration or in the atmosphere where a gas permeable culture vessel is placed may be within the range of 0.1–30% (v/v), preferably 0.5–20% (v/v). In the case of a culture jar, the aeration rate may be within the range of 0.0001–1 volume, preferably 0.001–0.1 volume per minute per volume of a jar capacity.

Under these conditions, stolons and axillary buds (the latter become stolons which then become tubers easily during a tuber formation step) are efficiently induced and propagated in a large number in the gaseous and liquid phases, especially in the liquid phase. When a carbon dioxide concentration or aeration rate is smaller than the aforementioned range, plants will show a normal growth form and, therefore, stolons will hardly be formed. In other words, buds elongated from axillary buds in the liquid phase may not become stolons but develop into an usual shoot form. The axillary buds contained in these shoots show low tuber forming ability.

On the contrary, plants will wither if a carbon dioxide concentration is excessively high (30% or higher). When an aeration rate is too high (1 volume or more per minute per unit volume of a vessel), an excess amount of carbon dioxide or a vigorous aeration will slow the growth of plants and elongation of stolons due to evaporation of a medium and over-humidity (liquid phase aeration) or excessive dryness (gas phase aeration) in the gaseous phase.

When a culture jar is used, carbon dioxide-enriched air may be supplied into a liquid phase and/or gaseous phase. Preferably, the gaseous phase may be supplied with carbon-dioxide-enriched air, while the liquid phase is aerated with an appropriate amount (ca. 0.001 to 0.05 vvm) of normal air.

Carbon dioxide may be applied at least for 1 hour a day, preferably 2 hours or longer a day in light periods during at least a part of the shoot propagation step. The carbon dioxide application may be carried out for 10 to 70 days, preferably 20 to 40 days.

Carbon dioxide treatment can be applied to any size of a plant or a plant piece: application of carbon dioxide may be started immediately after planting the plant or plant piece or after culturing them for a certain period of time according to the method known in the art.

When there is time that carbon dioxide is not applied, normal air may be supplied instead of carbon-dioxide-enriched air under similar conditions. When a culture jar is used and carbon dioxide is not applied, it is desirable that the liquid phase is aerated with an appropriate amount of normal air (0.001 to 0.1 vvm).

Tuber Formation Step (B)

A tuber induction medium contains at least a. carbon source as an essential element and comprises, but is not limited to, the same composition as that of a medium used in the step (A) or the same composition as that of a medium used in the step (A) plus an increased sugar concentration. A sugar concentration in the case of sucrose may be within the range from 5 to 15%, preferably from 6 to 10%. If necessary, an induction medium may be supplemented with 0.01 to 20 ppm of plant hormones such as 6-benzyladenine (BA), kinetin, zeatin, abscisic acid (ABA) and the Jike, and plant growth retardants such as cycocel (CCC), ancymidol and the like. After a shoot propagation medium is removed from a culture vessel of the shoot propagation step (A), a tuber induction medium is poured into the vessel. The volume of the medium should be an amount that at least a portion of induced and propagated stolons or a portion of stolons having an improved tuber forming ability during the step (A) is exposed to the gaseous phase. A relatively smaller amount of a medium as compared to that of a medium during the step (A), an amount which exposes many stolons and stems to a gaseous phase, is preferably used during the step (B). Stolons elongated during the step (A) already possesse high tuber forming ability independent of positions on the plants. Those stolons and stems elongated in the liquid phase can simultaneously form tubers efficiently, within a short period of time and independent of distance from the medium surface, when they are exposed to the gaseous phase in the step (B). In general, an amount of a tuber induction medium may be in the range of 5–80%, preferably 10–40%, of the volume of the step (A) medium.

Alternatively, the volume of a medium used in the step (A) may be reduced to a level that satisfies the conditions. A necessary amount of a concentrated solution of tuber-inducing components (i.e., sugar, aforementioned basal medium composition, plant hormones etc.) may be added to the medium. Instead of manipulating a medium volume, stolons in the liquid phase may be exposed to the gaseous phase by other means; lifting up the plant, laying it down, turning it upside down, or laying a vessel down if the culture vessel is tall, or changing the shape of a bag if the bag is used as a culture vessel. The pH of an induction medium may be in the range of 4–8, preferably 5–7.

Various light conditions may be employed. For example, a low illuminance of 100 to 1,000 lux may be applied within an appropriate photoperiodic range (4 to 24 hours), and a short-day condition (4 to 10 hours) may be applied within an appropriate range of illuminance (100 to 8,000 lux). To obtain good results, these two conditions, illuminance and photoperiod, may be used in combination, or tuber-forming parts of plants may be shaded. Dark conditions may also give good results. A large number of tubers can be formed without increasing sugar concentration in a medium, especially when a short-day condition is applied.

Culture temperature may be within the range from 5° to 30° C., preferably from 15° to 25° C. When a short-day condition is applied, temperature during the dark period may be adjusted to a level lower than that in the light period.

When an air-permeable vessel is used in this step, culture may preferably be carried out in an atmospheric environment which satisfies the aforementioned culture conditions. When a culture jar is used, the liquid phase is aerated as described in prior arts (e.g., an aeration rate of 0.001–0.1 vvm).

According to the process of the present invention, further improved results may be obtained when the step (B) is combined with the second embodiment of the present invention in which the relative humidity of the gaseous phase is lowered by aerating the gaseous phase during the tuber formation step. The optimum aeration rate may be within the range of 0.02–1, preferably 0.05–0.5 volume per minute per volume of a vessel capacity. The aeration rate may vary with various factors such as absolute volume of a medium, shape of a vessel, volume of plants in the gas phase, aeration rate supplied to a liquid phase, shape and the number of inlets for the gaseous phase aeration, and the like. Both quantity and quality of tubers are improved when the relative humidity of a gaseous phase becomes 90% or below by the aeration. If the aeration rate is smaller than the range described above, the aeration would result in an insufficient formation of tubers in a gaseous phase and, if the aeration rate is larger than the range, the aeration would cause withering of plants due to excessive dryness. When air is supplied into the liquid phase, the aeration rate may preferably be 0.05 vvm or below. Under these conditions, a decrease of the medium volume through evaporation may be negligible. Even if an aeration rate is increased to a level that reduces a medium volume, a greater number of the tubers may be formed by aerating a gaseous phase than by aerating a liquid phase alone.

The second embodiment of the present invention can be applied to plants produced by the prior art culture processes and results in remarkably desirable effects.

According to the process of the present invention, an artificial aeration in the gaseous phase during the tuber formation step may be replaced by other means which can reduce the relative humidity of the gaseous phase to 90% or below. Examples of such means include (1) utilization of a culture jar having a high ventilation capacity, (2) utilization of a substance which can prevent evaporation of water from a medium surface and (3) utilization of a culture jar in which once evaporated water from a medium surface can not go to the gaseous phase.

The culture period of a tuber formation step may be 10–50 days, preferably 20–40 days.

EXAMPLES

The present invention will be further described by the following Examples which are intended to illustrate the invention but are not intended to limit the scope of the invention.

Example 1

Effects of Aeration to the Gaseous Phase in the Culture Jar on the Positions and Efficiency of Tuber Formation at the Time of Tuber Formation Aseptic plants obtained from a potato plant (*Solanum tuberosum* L. cultivar Norin No. 1) by an apical meristem culture were used in this experiment.

Three plantlets, each having 5 nodes and some roots, were placed in 10 liters of an MS liquid medium supplemented with 3% sucrose, pH 5.8 (referred to as "shoot propagation medium" hereinafter), in a cylindrical culture jar (about 23 liter capacity; 27 cm in diameter and 40 cm in height), and were grown for 5 weeks to produce shoots under the conditions: temperature, 22° C.; illuminance, 6,000 lux; day light, 16 hours; and aeration, 30 ml/min in the liquid phase and 500 ml/min in the gaseous phase. During the culture, the plants. showed vigorous growth to a height of about 30 cm. The medium remained in the jar was then replaced by 10 liter of an MS liquid medium supplemented with 8% sucrose, pH 5.8 (referred to as "tuber induction medium" hereinafter) and induction of tubers was continued for additional 3 weeks at 22° C. in the dark. In this instance, aeration was carried out under two different conditions; (1) 1030 ml/min into the liquid phase alone (control plot) and (2) 30 ml/min into the liquid phase and 1,000 ml/min into the gaseous phase, in order to compare effects of these aeration conditions on the positions of tuberization on the plant and efficiency of tuber formation. In both shoot propagation and tuber formation steps, air supply into the gaseous phase was done through an inlet equipped at the top of the jar. The air outlet was positioned at a height of about 30 cm. The level of the medium surface in the jar at the end of the culture was almost the same in both plots, (1) and (2). The results are set forth in Table 1.

In the plot in which the gaseous phase was aerated, the following were observed: tubers were formed directly on the axillary buds in the gaseous phase; new white stems containing no chloroplast vigorously elongated from many axillary buds in both liquid and gaseous phases; and a large number of tubers were formed even on the gaseous-phase-exposed nodes of the new stems. In contrast, the following were observed in the control plot: tubers were scarcely formed on the axillary buds in the gaseous phase; a small number of white stems similar to ones described above were found but most of the apical buds were dead due to excessive moisture; and tubers were formed mostly on the axillary buds at the boundary area of the medium surface and at the area just above the surface. As a result, the number and weight of the tubers in the gaseous phase aeration plot were improved greatly (more than two times in comparison with the control plot). The position of the tubers in the gaseous phase aeration plot was different from those of the tubers in the control plot and more than 60% of the tubers were formed 5 cm or far away from the medium surface in the gaseous phase aeration plot. In addition, a large number of the tubers were formed at the position more than 10 cm away from the medium surface where no tuber was observed in the control plot. While most tubers in the control plot showed markedly enlarged lenticels and undesirable secondary growth, these problems were greatly improved in the gaseous phase aeration plot.

TABLE 1

| Aeration condition (ml/min) | | The number of tubers (upper row) and their weight (lower row) | | | | |
|---|---|---|---|---|---|---|
| Liquid phase | Gas phase | in terms of their formed positions on the plants | | | | |
| | | 0 to 5 cm* | 5 to 10 cm | 10 to 15 cm | 15 cm ~ | Total |
| 1030 | 0 | 162 | 59 | 0 | 0 | 221 |
| | | 211 (g) | 55 | 0 | 0 | 266 |
| 30 | 1000 | 168 | 194 | 75 | 57 | 494 |
| | | 224 (g) | 208 | 65 | 62 | 559 |

*Distance from medium surface after completion of culturing.

Example 2

Effects of Aeration to the Gaseous Phase in the Culture Jar on Tuber Formation Efficiency and the Quality of Tubers at the Time of Tuber Formation An aseptic potato plant (*Solanum tuberosum* L. cultivar Russet Burbank) was cut into small pieces. Five pieces, each having 5 nodes and some roots, were placed in 3 liter of a shoot propagation medium (alteration: sucrose concentration was 2%) in a culture jar (about 8 liter capacity, 20 cm in diameter and 24 cm in height) and were cultured for 5 weeks to produce shoots under the conditions: temperature, 22° C.; illuminance, 6,000 lux; day light, 16 hours; and aeration, 30 ml/min in the liquid phase and 100 ml/min in the gaseous phase. The used medium in the jar was replaced with 3 liter of a tuber induction medium. The gaseous phase aeration was then increased to 1 liter/min and tuberization was carried out for 3 weeks at 22° C. in the dark. Control plot was prepared and treated according to the procedure described above except that the aeration at the time of the tuber induction was applied only to the liquid phase at a rate of 30 ml/min. The results are set forth in Table 2.

TABLE 2

| Test plot | Total number of tubers | Total weight of tubers(g) | Damage on epidermis |
|---|---|---|---|
| Gaseous phase aeration | 149 | 248 | ± |
| Control | 99 | 221 | +++ |

The tuber was grown by the same process as described in Example 1. Tubers were mainly formed at the gaseous phase area in the gaseous phase aeration plot, while tubers were mostly formed at the gas/liquid boundary area in the control plot. The gaseous phase aeration plot exceeded the control plot in total number and weight of the tubers. In addition, a considerable difference was found in the degree of damage on the epidermis: most of the tubers formed in the control plot showed markedly enlarged lenticels and significant epidermal damage caused by the excessive humidity or by the contact with the medium, as well as undesirable secondary growth, while these problems were negligible in the gaseous phase aeration plot. The difference in quality between the tubers of the gaseous phase aeration plot and those of the control plot was more clearly found during the storage of the tubers: more than half of the tubers obtained from the control plot deteriorated due to the excessive evaporation of moisture during the storage at a low temperature and were unsuitable for the use in cultivation, while the tubers obtained from the gaseous phase aeration plot were hardly changed in quality during the storage.

As is evident from the results, the process of the invention in which tubers are formed in a gaseous phase has a remarkable effect on tuber quality improvement of certain potato cultivars such as Russet Burbank which forms humidity-sensitive tubers (susceptible to epidermal damage).

Example 3

Effects of Relative Humidity at the Gaseous Phase in the Culture Jar on Tuber Formation at the Time of Tuber Formation Shoots were grown in 3 liters of a shoot propagation medium in a 16 liter culture jar (20 cm in diameter and 48 cm in height) under the same conditions as in Example 1 until the shoots reached a height of about 20 cm. After the growth of the shoots, the medium remained in the jar was replaced by 3 liter of a tuber induction medium and the culture was continued at 22° C. in the dark at an aeration rates of 30 ml/min in the liquid phase and 1,000 ml/min in the gaseous phase. Effects of the relative humidity at the gaseous phase in the culture jar on tuber formation were tested by varying humidity levels by changing the position of the aeration inlet: inlet (1) the supply of air from a position close to the medium surface (about 5 cm above the surface) and inlet (2) the supply of air from the top side of the jar. In both cases, air was directed toward a medium surface. The relative humidity inside the jar (which was measured at the air outlet equipped at the top of the culture jar) and tuberization under different humidities were examined. The results are set forth in Table 3.

TABLE 3

| Position of gas phase aeration | Relative humidity at air outlet | The number of tubers in terms of their formed positions on the plants | | | | |
|---|---|---|---|---|---|---|
| | | 0–5 cm* | 5–10 cm | 10–15 cm | 15 cm ~ | Total |
| (1) Near the medium surface | 100% | 106 | 30 | 5 | 0 | 141 |
| (2) From the top of culture jar | 60.1% | 67 | 48 | 26 | 69 | 210 |

*Distance from medium surface after completion of culturing.

In the case of the inlet (2) in which air was supplied through an inlet near the top of the culture jar, white stems elongated vigorously as were observed in Example 1 and many of them reached the top of the jar and formed many tubers. On the contrary, tubers were seldom formed in the area above the medium surface in the case of the inlet (1), in which air was supplied through the inlet close to the medium surface. Fine drops of water were observed at the top of the culture jar in the case of the inlet (1). In addition, the relative humidity measured at the air outlet was markedly low in the case of the inlet (2), as compared with that of the inlet (1). These results indicate that tuber formation can be improved by reducing relative humidity at the gaseous phase area in a jar where tubers are formed.

Reference Example

Evaluation of field productivity of tubers prepared by gaseous phase aeration method Tubers obtained by the process of the present invention were tested for sprouting, growth and yield of tubers in the field in Hokkaido (Kenbuchi-cho, Kamikawagun). The tubers were prepared in the same manner as in Example 1. After the tubers were stored for a certain period of time at a low temperature (2° to 4° C.) in the dark, the tubers were divided by size and duration of storage and were planted and cultivated according to the local practice except that the tubers were planted in slightly shallower depth. When the weight of the tuber was in the range of 0.1–0.5 g, the tuber was initially sprouted and the seedling was raised in the paper pot (diameter of 5 cm and a length of 7.5 cm) in the greenhouse and then planted in the field. The results are set forth in Table 4.

Considerably low sprouting ratio was observed only in the case of the 2 month storage plot, which was thought to be due to the short storing period that was not sufficient for the breakage of dormancy prior to planting. The sprouting ratio was high both in the 5 month and 9 month storage plots independent of the size of the tubers. In general, the initial growth after sprouting in these plots was slightly inferior to that in the control plot, but the growth returned to normal thereafter. The final yield in the test plots where the tubers of different sizes were planted was almost the same as, or higher in some test plots. than, that of the control plot. It was confirmed that the tubers prepared by the process of the present invention possessed high growth and production ability.

liquid phase. During the culture, the plants branched mainly in the liquid phase as they vigorously grew and formed a large number of axillary buds. Some of the shoots elongated into the gaseous phase, but stolons did not develop at. this stage. Air enriched with 10% carbon dioxide was then supplied into the gaseous phase at an aeration rate of 100 ml/min, without changing the liquid phase aeration condition, and the culture was continued for another 3 weeks. During the culture, additional growth of the plants, as well as the vigorous induction and propagation of the stolons from the axillary buds were observed mainly in the liquid phase. Most of the stolons elongated toward the wall of the culture jar, showing their plagiotropismic nature, but some of them elongated slightly upward and some of these stolons reached the gaseous phase. The plant in the liquid medium finally formed a unique structure covered with stolons. Control plot, a plot where air without carbon dioxide enrichment was supplied into the gaseous phase, was prepared. In the control plot, no distinct induction and propagation of stolons were observed. In addition, the plant showed a significant difference in the plant morphology from the plant in the carbon-dioxide-applied plot. Thereafter, the medium remained in the jar was replaced by 1.5 liter of a tuber induction medium and the culture was continued for additional 4 weeks at 20° C. under continuous dark condition. Air without carbon dioxide enrichment was

TABLE 4

| Storage (month) | Size of seed tubers[1] | Number of seeds tested | Sprouting rate[2] (%) | Number of stems per seed[3] | Yield[4] (g/seed) | Yield of marketable tubers[5] (g/seed) | Yield of marketable tubers (t/10a) | Number of marketable tubers per seed | Starch value (%) |
|---|---|---|---|---|---|---|---|---|---|
| 2 | small | 30 | 16.7 | 1.1 | 970 | 728 | 3.4 | 7.7 | 10.7 |
|   | medium | 30 | 6.7 | 1.4 | 1013 | 820 | 3.8 | 6.5 | 12.3 |
|   | large | 32 | 12.5 | 1.3 | 1207 | 1046 | 4.8 | 8.2 | 13.6 |
| 5 | paper pot | 60 | — | 1.1 | 1108 | 932 | 4.3 | 10.9 | 13.3 |
|   | small | 30 | 93.3 | 1.5 | 1324 | 1203 | 5.6 | 12.1 | 11.8 |
|   | medium | 30 | 90.0 | 1.4 | 1106 | 1006 | 4.7 | 9.2 | 14.4 |
|   | large | 32 | 93.8 | 1.2 | 1324 | 1150 | 5.3 | 10.7 | 13.4 |
| 9 | paper pot | 60 | — | 1.6 | 1207 | 1029 | 4.8 | 11.1 | 12.4 |
|   | small | 30 | 100.0 | 1.5 | 1120 | 985 | 4.6 | 10.7 | 12.1 |
|   | medium | 30 | 96.7 | 1.8 | 1286 | 1179 | 5.5 | 10.7 | 15.1 |
|   | large | 32 | 93.8 | 2.7 | 1317 | 1249 | 5.8 | 11.2 | 14.2 |
| Control[6] |   | 60 | 83.3 | 4.2 | 1211 | 1140 | 5.3 | 0.9 | 14.5 |

[1]Paper pot, 0.1 to 0.5 g; small, 0.5 to 1 g; medium, 1 to 5 g; and large, 5 to 10 g. Planting density of 72 cm × 30 cm was employed in each size plot.
[2]Examined 4 weeks after planting.
[3]Average value of 12 seed tubers in each plot.
[4]Total yield/number of individuals tested in each plot.
[5]More than 40 g.
[6]Usual seed potatoes (40 to 120 g).

Example 4
Effect of Carbon Dioxide Application in the Culture Jar on the Subsequent Tuber Formation As test materials used in this experiment, aseptic plants were prepared from a apical meristem culture of a potato plant (*Solanum tuberosum* L. cultivar Bintje was obtained from the Gene Bank of Ministry of Agriculture, Forestry and Fisheries through the Bio-oriented Technology Research Advancement Institution).

Three plants, each having 5 nodes and some roots, were planted in 5 liters of a shoot propagation medium (see Example 1) in a 8 liter culture jar (20 cm in diameter and 24 cm in height). The culture jar was placed in an incubator equipped with lights to illuminate the jar from every direction. The planted materials were pre-cultured for 3 weeks under conditions: temperature, 20° C.; illuminance, 7,000 lux, continuous illumination; and aeration, 30 ml/min in the supplied to the liquid phase at an aeration rate of 30 ml/min and to the gaseous phase at 1,000 ml/min in both carbon-dioxide-applied plot and control plot. In the carbon-dioxide-applied plot, the majority of the stolons formed in the liquid phase were exposed to the gaseous phase by the medium replacement. The results are set forth in Table 5.

TABLE 5

| Test plot | Total number of tubers | Total weight (g) | Number of 0.5 g or heavier tubers | Average weight (g) per one tuber |
|---|---|---|---|---|
| Carbon dioxide-applied plot | 722 (656)* | 441 (315) | 280 (354) | 0.61 (48) |

TABLE 5-continued

| Test plot | Total number of tubers | Total weight (g) | Number of 0.5 g or heavier tubers | Average weight (g) per one tuber |
|---|---|---|---|---|
| Control plot | 110 (100) | 140 (100) | 79 (100) | 1.27 (100) |

*Comparative value based on the control plot.

In the carbon-dioxide-applied plot, (1) most of the gas-phase-exposed stolons almost simultaneously started tuberization at their tip parts, regardless of their distance from the medium surface, at the second day after the medium exchange, and then (2) tubers were directly formed on the nodular portions of the stolons or on the newly induced stolons. Thereafter, (3) the nodular portions of the other stems developed white stems (as was observed in Example 1) and stolons, and formed tubers.

During the tuber formation, the plant in the carbon-dioxide-applied plot produced a unique structure. The structure was specifically found in the process of the present invention, characterized in that the entire gaseous-phase-exposed parts of a plant was full of tubers. Conversely, in the control plot, tubers were formed only through the above tuberization step (3), and the start of tuberization was much slower as compared to that of the carbon-dioxide-applied plot. As a result, the carbon-dioxide-applied plot exceeded the control plot in the total number and weight of the tubers per culture jar. Though the average weight per tuber was small in the carbon-dioxide-applied plot, it is evident from the foregoing Reference Example that normal sprouting, growth and yield can be attained by the use of such small size tubers.

Example 5

Effect of Carbon Dioxide Application in the Culture Jar on the Subsequent Tuber Formation Shoots of Russet Burbank were propagated for 3 weeks in the same manner as in Example 2. Two liters of a shoot propagation medium containing 2% sucrose were added to the propagation culture. The gaseous phase was aerated with air enriched with 2% carbon dioxide. The culture was continued for 3 weeks at 20° C. under a continuous day light condition of 6,000 lux to promote induction and elongation of stolons. The aeration condition in the control plot was the same condition as in Example 2. After medium supplement, the culture was carried out in an incubator in which illumination can be made from every direction. Thereafter, the medium remained in the jar was replaced by 1.5 liter of a tuber induction medium and induction of tubers was carried out for another 4 weeks at 20° C. in the dark. In both carbon-dioxide-applied plot and control plot, the jar was newly equipped with an additional air inlet at diagonal position to the previous one for gaseous phase aeration, and the gaseous phase aeration was aerated at a rate of 1,000 ml/min through each of the two inlets, while the liquid phase was aerated at a rate of 30 ml/min. The results are set forth in Table 6.

TABLE 6

| Test plot | Total number of tubers | Total weight of tubers(g) | Average weight per tuber (g) |
|---|---|---|---|
| Carbon dioxide applied plot | 316 (247)* | 611 (320) | 1.93 (130) |
| Control plot | 128 (100) | 191 (100) | 1.49 (100) |

*Comparative ratio to the control plot.

As is evident from Table 6, the total number and weight of tubers of cultivar Russet Burbank significantly increases as is observed in cultivar Bintje as in Example 4, suggesting effectiveness of carbon dioxide application at the time of shoot propagation. The rate of increase in total weight of the tubers in the carbon-dioxide-applied plot as compared to that of the tubers in the control plot exceeded the rate of increase in the total number of the tubers, which results in a greatly improved average weight per tuber. The tubers thus obtained in both carbon-dioxide-applied plot and control plot showed excellent quality without having enlarged lenticels or epidermal injury. This was because tubers formed mainly in the gaseous phase in both plots.

Example 6

Effect of Carbon Dioxide Application in the Culture Jar under Long Day and Low Temperature in Dark Period on Induction and Propagation of Stolons and the Subsequent Tuber Formation Aseptic Bintje and Russet Burbank plants maintained at 20° C. under an illuminance of 6,000 lux and a day light length of 16 hours, were used as test materials. Five plants, each having 5 nodes and some roots, were planted in 3 liters of a shoot propagation medium (2% sucrose concentration) in an 8 liter culture jars. The culture jar was placed in an incubator equipped with lights to illuminate the jar mainly from bottom side. The plant was cultured under conditions of: illuminance, 6,000 lux; day light, 16 hours; temperature during light period, 22° C.; and temperature during dark period, 10° C. The number of stolons formed was counted 6 weeks after the culture. Air enriched with 2% carbon dioxide was supplied into the gaseous phase at an aeration rate of 100 ml/min, and normal air into the liquid phase at a rate of 30 ml/min. Control plots were prepared by the same procedure as described above except that the gaseous phase was aerated with normal air (control plot II) or that the gaseous phase was aerated with normal air and culture temperature was adjusted to 22° C. regardless of light or dark periods (control plot I).

Propagation of shoots and stolons of Bintje was performed as described above. The medium remained in the jar was replaced by 1 liter of a tuber induction medium. The number of tubers formed at 20° C. in the dark was examined 4 weeks later. Normal air was supplied into the gaseous phase at an aeration rate of 1,000 ml/min and into the liquid phase at a rate of 30 ml/min in both carbon dioxide-applied plot and control plot I. Many of the stolons vigorously grown and branched in the liquid phase at the time of carbon dioxide application were exposed to the gaseous phase by the medium replacement.

The study results of stolons are shown in Table 7 and the number of tubers formed are set forth in Table 8.

TABLE 7

| Cultivar | Carbon dioxide applied plot | Control plot I | Control plot II |
|---|---|---|---|
| Bintje | 1794* | 0 | 0 |
| Russet Burbank | 638 | 0 | 0 |

*The number of stolons formed.

In the carbon-dioxide-applied plot, both Bintje and Russet Burbank plants kept growing shoots 2 weeks after the start of the culture, and then started elongating stolons from their axillary buds mainly in the liquid phase, followed by vigorous propagation of stolons. On the contrary, no stolon developed in both control plots, I and II. The difference between the plots showed striking effects of carbon dioxide application. In comparison with the stolons observed in Example 4, those observed in this experiment showed unique properties such as significant plagiotropismic nature and numerous branching.

When the test materials were induced to have stolons by carbon dioxide application prior to planting, the stolons were vigorously propagated immediately after planting. The pre-treatment of the plants with carbon dioxide gave better results.

TABLE 8

| Test plot | Total number of tubers | Total weight of tubers(g) | Average weight of tuber (g) |
|---|---|---|---|
| Carbon dioxide applied plot | 315 (217)* | 231 (229) | 0.73 (104) |
| Control plot I | 145 (100) | 101 (100) | 0.70 (100) |

*Comparative ratio to the control plot.

As was observed in Example 5, stolons in the carbon-dioxide-applied plot almost simultaneously started forming tubers on the tips immediately after being exposed to the gaseous phase, independent of the distance from the medium surface. In addition, already branched secondary stolons also formed tubers within a short period of time. As a result, the difference in the degree of tuber formation between the carbon dioxide-applied plot and the control plot became significant.

Example 7
Effect of Timing of Carbon Dioxide Application on Induction and Propagation of Stolons and the Subsequent Tuber Formation Aseptic Bintje plants was cut into pieces having a node with a length of about 1 cm, and a set of three nodes was planted in 400 ml of a shoot propagation medium in a 500 ml conical flask. The flask was sealed with a sheet of aluminum foil equipped with an air permeable filter (Trade name, PF Microfilter; manufactured by Shibata Hario Glass Co., Ltd.). The nodes were statically cultured under the following three different conditions in order to examine the degrees of induction and propagation of stolons: (A) Control; 6 week culture at 20° C., with continuous illumination at an illuminance of about 7,000 lux, without carbon dioxide application (about 0.03% carbon dioxide (v/v) in air); (B) 6 week culture : under the same conditions as in (A) except that the culture was carried out in an atmosphere enriched with 2% (v/v) carbon dioxide; and (C) 3 week culture under the same conditions as in (A) followed by additional 3 weeks of culturing under the conditions of (B). In each test plot, illumination was made from all the directions. After the completion of the culture, the medium remained in each flask was replaced by 100 ml of a tuber induction medium, and the culture was continued for additional 4 weeks at 20° C. in the dark in order to examine degree of tuberization in each test plot. The results are set forth in Table 9.

TABLE 9

| | | Tuberization efficiency* | | |
|---|---|---|---|---|
| Conditions/ test items | Propagation of stolons | Number of tubers | Total weight (g) | Weight (g/tuber) |
| (A) | – | 21.8 (100)** | 16.7 (100) | 0.77 (100) |
| (B) | +++ | 66.5 (305) | 29.1 (174) | 0.44 (57) |
| (C) | +++ | 73.5 (337) | 31.9 (191) | 0.43 (56) |

*Average value of 4 repetitions per one vessel in each test plot.
**Comparative ratio to the control plot.

As is evident from Table 9, carbon dioxide application is also effective even when culture is carried out in a vessel placed in an carbon dioxide-enriched atmosphere. While no propagation of stolons was found in the control plot (A), vigorous induction and propagation of stolons were observed in the plot (B) in which carbon dioxide application was started simultaneously at the beginning of the culture, and in the plot (C) in which carbon dioxide application was started in the middle of the culture. The tuberization efficiency was also improved: test plots, (B) and (C), showed more than three times higher tuber numbers and nearly two times higher total tuber weights as compared with the control plot (A). The significant difference in the timing of tuberization was also found between the control plot and the carbon dioxide-applied plots: while formation of tubers in the control plot (A) started about 5 days after the medium replacement and the number of the tubers increased gradually during the subsequent 3 weeks, the majority of the tubers in the carbon dioxide-applied plots (B) and (C) formed simultaneously by development of the tips of the stolons within a short period, from about 2 to 14 days after the medium replacement. The differences in timing and duration of carbon dioxide application between plots (B) and (C) showed no significant effect on the propagation of stolons and formation of the tubers.

The average weight per tuber of both carbon dioxide-applied plots was lower than that of the control plot. The low average weight, however, did not reduce the effect of carbon dioxide application on the improvement of tuberization efficiency. As is described in the Reference Example, a small size tuber (around 0.1 g) can normally sprout, grow and reproduce tubers.

Example 8
Effect of Medium Volume at the Time of Tuber Formation Step on Formation of Tubers from Stolons Propagated under Carbon-Dioxide-Applied Conditions Two hundred milliliters of a shoot propagation medium was placed in a 380 ml cylindrical culture vessel (6 cm in diameter and 15 cm in height) to carry out the following tests. The material to be planted and the carbon-dioxide-applied culture conditions were the same as those described in Example 7-(B). Fifth week after the begining of culture when stolons showed vigrous propagation in both gaseous and liquid phases, the medium remained in the vessel was replaced by (1) 50 ml, (2) 100 ml and (3) 200 ml of a tuber induction medium. The culture was continued under the same conditions as in Example 7 in order to examine the relationship between a medium volume and tuberization efficiency. The results are as set forth in Table 10.

TABLE 10

| Medium volume for shoot propagation (ml) | Medium volume for tuber formation (ml) | Tuberization efficiency* | | |
|---|---|---|---|---|
| | | Number of tubers | Total wt (g) | Weight (g/tuber) |
| 200 | (1) 50 | 44.5 (291)** | 13.2 (106) | 0.30 (37) |
| | (2) 100 | 54.0 (353) | 16.3 (131) | 0.30 (37) |
| | (3) 200 | 39.5 (258) | 10.4 (84) | 0.26 (32) |
| 200 (control)*** | 50 | 15.3 (100) | 12.4 (100) | 0.81 (100) |

*Average value of 4 repetitions per one vessel in each test plot.
**Comparative ratio to the control plot.
***Culture under atmospheric condition (carbon dioxide concentration, 0.03%).

As was observed in Example 7, carbon dioxide application showed markedly good effect on the number of tubers formed per vessel. These results indicate that the number and weight of the tubers formed can be improved by reducing the medium volume at the time of a tuber formation step to a level lower than the medium volume used in a shoot propagation step. The majority the tubers were formed on the stolons which were elongated into the liquid phase during the shoot propagation step and which were then exposed to the gaseous phase during the tuber formation step.

Example 9
Effects of Carbon Dioxide Concentration on Induction and Propagation of Stolons and the Subsequent Tuber Formation In order to examine the effect of carbon dioxide concentration, the same procedure as described in Example 8-(1) was carried out except that a carbon dioxide content in the atmosphere was 1, 5 and 10%. The results are set forth in Table 11.

TABLE 11

| Carbon dioxide concentration % (v/v) | Growth of stolons | Tuberization efficiency* | | |
|---|---|---|---|---|
| | | Number of tubers | Total wt (g) | Weight (g/tuber) |
| 1 | +++ | 30.3 (198)** | 10.0 (81) | 0.33 (41) |
| 5 | +++ | 62.0 (405) | 16.4 (132) | 0.26 (32) |
| 10 | ++ | 34.0 (222) | 12.5 (101) | 0.37 (46) |
| Control*** | − | 15.3 (100) | 12.4 (100) | 0.81 (100) |

*Average value of 4 repetitions per one vessel in each test plot.
**Comparative ratio to the control plot.
***Culture under atmospheric condition (carbon dioxide concentration, 0.03%).

The number of tubers per vessel, which shows the most typical effect of carbon dioxide application, was improved greatly in all test plots compared to the control plot. Five percent carbon dioxide application plot, which showed the highest tuber number per vessel, was about four times higher than the control plot. The 1% and 10% application showed almost the same effect.

Example 10
Effects of Duration of Carbon Dioxide Application Per Day under Continuous Light Illumination on the Subsequent Tuber Formation In order to examine the effect of duration of carbon dioxide, the same procedure described in Example 7-(C) was carried out except that carbon dioxide was applied for (1) 2 hours, (2) 6 hours or (3) 10 hours per day, and no carbon dioxide was applied for the rest hours of the day under continuous illumination of light. The results are set forth in Table 12.

TABLE 12

| Duration of carbon dioxide application | Growth of stolons | Tuberization efficiency* | | |
|---|---|---|---|---|
| | | Number of tubers | Total wt (g) | Weight (g/tuber) |
| 2 hours | + | 41.0 (169)*** | 16.5 (97) | 0.40 (57) |
| 6 hours | + | 54.3 (223) | 19.8 (116) | 0.37 (53) |
| 10 hours | ++ | 50.3 (207) | 22.6 (133) | 0.45 (64) |
| 24 hours | +++ | 83.5 (344) | 27.2 (160) | 0.33 (47) |
| Control*** | − | 24.3 (100) | 17.0 (100) | 0.70 (100) |

*Average value of 4 repetitions per one vessel in each test plot.
**Comparative ratio to the control plot.
***Culture under atmospheric condition (carbon dioxide concentration, 0.03%).

The effects of carbon dioxide application under continuous illumination were clearly observed even in a short period (2 hours) of carbon dioxide application. The effects increased as the application period was extended.

Example 11
Effects of Duration of Carbon Dioxide Application Per Day during Light Period under Conditions (Short Day, Low Temperature in Dark Periods) on the Subsequent Tuber Formation The same procedure described in Example 7-(C) was carried out except that culture was carried out under short day (10 hours) and low temperature (10° C.) in dark period (20° C. for light period) during the latter half (3 weeks) of shoot propagation, and that carbon dioxide application was carried out for (1) 2 hours, (2) 6 hours or (3) 10 hours during each light period. The results are set forth in Table 13.

TABLE 13

| Duration of carbon dioxide application | Growth of stolons | Tuberization efficiency* | | |
|---|---|---|---|---|
| | | Number of tubers | Total wt (g) | Weight (g/tuber) |
| 2 hours | +++ | 38 (100)** | 20.2 (240) | 0.53 (241) |
| 6 hours | +++ | 67 (176) | 33.8 (402) | 0.50 (227) |

TABLE 13-continued

| Duration of carbon dioxide application | Growth of stolons | Tuberization efficiency* | | |
|---|---|---|---|---|
| | | Number of tubers | Total wt (g) | Weight (g/tuber) |
| 10 hours | +++ | 78 (205) | 30.4 (362) | 0.39 (177) |
| Control*** | ++ | 38 (100) | 8.4 (100) | 0.22 (100) |

*Average value of 4 repetitions per one vessel in each test plot.
**Comparative ratio to the control plot.
***Culture under atmospheric (carbon dioxide concentration, 0.03%) and short-day/low temperature conditions.

Elongation of stolons was observed even in the control plot which was cultured under the short-day/low temperature conditions, but the carbon-dioxide-applied plots exceeded the control plot in the number and thickness of the stolons. The effects of carbon dioxide on the tuber formation became evident in the total weight of tubers per vessel produced by the 2 hours/day treatment and in the number of tubers produced by the 6 hours/day treatment.

Effects of the Invention

The present invention provides a process for producing potato tubers having properties such as improved storage and cultivation ability, in which potato tubers can be produced more easily and in quantities as compared with the prior art process.

What is claimed is:

1. A process for producing tubers from a tuber-forming plant belonging to the genus Solanum in a culture vessel comprising the steps of:
   (a) performing a shoot propagation step to induce and propagate shoots and stolons; and
   (b) performing a tuber formation step on said stolons with the tuber formation step comprising:
      i) placing said stolons in a medium comprising a carbon source;
      ii) exposing a portion of said stolons of step i) to a gaseous phase; and
      iii) aerating said gaseous phase to reduce the relative humidity of the atmosphere of the culture vessel under conditions sufficient to induce the formation of tubers on said stolons.

2. A process for producing tubers from a tuber-forming plant belonging to the genus Solanum in a culture vessel comprising the steps of:
   a) performing a shoot propagation step to induce and propagate shoots and stolons; and
   b) performing a tuber formation step on said shoots with the tuber formation step comprising:
      i) placing said shoots in a medium comprising a carbon source;
      ii) exposing a portion of said shoots of step i) to a gaseous phase; and
      iii) aerating said gaseous phase to reduce the relative humidity of the atmosphere of the culture vessel under conditions sufficient to induce the formation of tubers on said shoots.

3. A process for producing tubers from a tuber-forming plant belonging to the genus Solanum comprising the steps of:
   (a) culturing a plant piece having at least one bud in a culture vessel containing a liquid medium comprising:
      i) a carbon source and
      ii) inorganic salts;
   (b) exposing said plant piece of step (a) to alternating periods of light and dark while the plant piece contacts the medium;
   (c) exposing said plant piece to carbon dioxide during at least one light period of step (b) to induce and propagate shoots and stolons from said plant piece;
   (d) culturing said stolons of step (c) in a liquid medium containing a carbon source; and
   (e) exposing at least a portion of said stolons to a gaseous phase during step (d) under conditions sufficient to induce the formation of tubers on said stolons.

4. The process for producing tubers according to claim 3 therein in step (c) said plant piece is exposed to said carbon dioxide by aerating said liquid medium and/or said gaseous phase with a stream of gas containing approximately 0.1–30% (v/v) of carbon dioxide.

5. The process for producing tubers according to claim 3 wherein in step (c) said carbon dioxide is applied to said plant piece at an aeration rate from 0.0001 to 1 volume per minute per volume of the culture vessel capacity.

6. The process for producing tubers according to claim 3 wherein the gaseous phase of step (e) is aerated to reduce the relative humidity thereof.

7. The process for producing tubers according to claim 6 wherein, in step (c), said plant piece is exposed to said carbon dioxide by aerating said liquid medium and/or said gaseous phase with a stream of gas comprising approximately 0.1–30% (v/v) carbon dioxide.

8. The process for producing tubers according to claim 6 wherein said carbon dioxide is applied to said stolons at an aeration rate from 0.0001 to 1 volume per minute per volume of the culture vessel capacity.

* * * * *